(12) United States Patent
In et al.

(10) Patent No.: US 11,751,709 B2
(45) Date of Patent: Sep. 12, 2023

(54) APPARATUS WITH CAPABILITY OF PRODUCING SCENT AND PROVIDING OTHER FEATURES

(71) Applicants: Stella In, Germantown, MD (US); Hyunjeung In, Germantown, MD (US)

(72) Inventors: Stella In, Germantown, MD (US); Hyunjeung In, Germantown, MD (US)

( * ) Notice: Subject to any disclaimer, the term of this patent is extended or adjusted under 35 U.S.C. 154(b) by 0 days.

(21) Appl. No.: 17/505,447

(22) Filed: Oct. 19, 2021

(65) Prior Publication Data

US 2022/0202225 A1 Jun. 30, 2022

Related U.S. Application Data

(60) Provisional application No. 63/133,199, filed on Dec. 31, 2020.

(51) Int. Cl.
| | |
|---|---|
| *A47G 33/06* | (2006.01) |
| *A47G 33/08* | (2006.01) |
| *A61L 9/12* | (2006.01) |

(52) U.S. Cl.
CPC ......... *A47G 33/0854* (2013.01); *A47G 33/06* (2013.01); *A47G 33/0818* (2013.01); *A61L 9/12* (2013.01); *A47G 2033/0827* (2013.01); *A61L 2209/12* (2013.01)

(58) Field of Classification Search
CPC ............... A47G 33/06; A47G 33/0854; A47G 2033/0827
See application file for complete search history.

(56) References Cited

U.S. PATENT DOCUMENTS

| | | | |
|---|---|---|---|
| 9,883,566 B1* | 1/2018 | Chen | F21V 23/001 |
| 2011/0198409 A1* | 8/2011 | Gorman | A47G 33/06 |
| | | | 239/34 |
| 2014/0334134 A1* | 11/2014 | Loomis | A41G 1/005 |
| | | | 362/123 |
| 2019/0349213 A1* | 11/2019 | Shive | G05B 15/02 |

* cited by examiner

*Primary Examiner* — Adam Krupicka
(74) *Attorney, Agent, or Firm* — Ichthus International Law PLLC

(57) ABSTRACT

An apparatus is provided including a base, a main trunk body coupled to the base, and a plurality of branches coupled to the main trunk body. The apparatus includes a plurality of scent component devices coupled to the main trunk body or the plurality of branches, where the plurality of scent component devices are disposed in receiving portions of the main trunk body or the plurality of branches. Further, each scent component device may be inserted into the receiving portions of the main trunk body or the branches, where the scent component device is configured to receive one or more scent modules including a scent material. When the scent component device is activated, the scent component device releases or diffuses a distinct scent using the scent material into an area that the apparatus is disposed.

16 Claims, 6 Drawing Sheets

APPARATUS WITH CAPABILITY OF PRODUCING SCENT AND PROVIDING OTHER FEATURES

CROSS-REFERENCE TO RELATED APPLICATION(S)

The present application claims the benefit of U.S. Provisional App. Ser. No. 63/133,199, filed on Dec. 31, 2020, the entire content of which is incorporated herein by reference.

TECHNICAL FIELD

The present disclosure relates to an apparatus with enhanced features, in particular, artificial trees and/or plants with natural scent and others.

BACKGROUND

During the Christmas season, people often use freshly cut pine trees for holiday decorative purposes, celebrating the seasonal occasion. Surrounding ourselves with nature can have a very positive effect on our wellbeing and productivity. Besides decorative use, it has been proven that pleasant scents from certain species of plants and trees, e.g., pine trees, can have a very positive emotional influence on people. Evergreen trees, such as pine trees, produce not only a pleasant smell but chemical compounds, such as flavonols and bioflavonoids, that have a variety of positive effects on human body.

Researchers have found that smelling pleasant fragrances can lift our moods, making us more amiable and even boosting productivity. According to some studies, it has been shown that taking a so called "forest bath" (e.g., taking a walk or hike in the forest) will reduce stress and anxiety, lowering risk for depression. Some choose to bring home pine branches or use pine fragrances in candles or oil diffusers for their scent. Cinnamon is another scent that can have a positive effect on cognitive tasks, enhancing memory and alertness. Many studies showed that cinnamon improved participants' scores on tasks related to attentional processes, virtual recognition memory, working memory, and visual motor response speed. Similar to cinnamon, the scent of peppermint has been shown to increase alertness, boost motivation and increase confidence, speed and energy. Peppermint essential oils also improve memory, concentration and clear thinking. Further, inhaling diffused lavender essential oil can stabilize a mood and help with depression and emotional stress, as well as help to relieve headaches and migraines.

A type of diffuser that may be used to release fragrance is the reed diffuser. This diffuser uses a reed, which has a porous structure that provides a controlled rate of fragrance release, as the fragrance is diffused along the entire length of the reed. Another type of diffuser includes the ultrasonic diffuser.

People love the smell of freshly cut trees in the air and the smell fills the people with a seasonal joy. As such, every year people freshly cut and use pine trees as Christmas trees, which requires growing and/or cutting trees for this purpose. After the season, people usually throw away or dispose of Christmas trees, which is not environmentally friendly. To mitigate this, there are artificial trees made of plastics or other materials, but these artificial trees do not come with scent. Many people miss the scent of the freshly-cut pine trees, whether it is because of preference or possible positive effects. Further, the artificial trees and/or plants are disposed in an environment to make the place more like a natural place, without offering any other features.

Thus, there is still a need for providing advanced means for replacing freshly-cut trees or plants with artificial trees or plants capable of producing scent and providing other enhanced features.

SUMMARY

The present technology described herein provides an apparatus for providing one or more enhanced capabilities, for example, artificial trees or plants with various enhanced features such as natural scent, nature sounds, surveillance capability, etc.

In one embodiment of the present technology, an apparatus include a base, a main trunk body coupled to the base, a plurality of branches coupled to the main trunk body, and a plurality of scent component devices each coupled to the main trunk body or the plurality of branches. The plurality of scent component devices are disposed in receiving portions of the main trunk body or the plurality of branches.

In another aspect of the present disclosure, the plurality of scent component devices may be configured to be removable and include electrical contact so that when the scent component devices are inserted into the receiving portions of the main trunk body or the plurality of branches they are electrically connected via the electrical contact.

In another aspect of the present disclosure, each of the plurality of scent component devices may comprise a body including a first portion and a second portion, where the body of the scent component device is configured to be inserted into the receiving portions of the main trunk body or the branches. Further, the first portion of the scent component device may be configured to include various components or electronics thereof, and the second portion of the scent component device may be configured to receive one or more scent modules including a scent material. When the scent component devices are inserted and activated, the scent component devices may be configured to produce or release a distinct scent from the scent material, diffusing the scent into an area where the apparatus is disposed.

In still another aspect of the present disclosure, each of the scent modules may include a cartridge form and the distinct scent may be a pine scent.

In still another aspect of the present disclosure, the apparatus may be further configured to include one or more speakers coupled to the base or the main trunk body of the apparatus, where the one or more speakers may be configured to communicate with a remote device over a network.

In another aspect of the present disclosure, in the example above, the one or more speakers may be wireless speakers capable of communicating with the remote device using WiFi, Bluetooth, or other wireless communications technology.

In another aspect of the present disclosure, the apparatus may be further configured to include a control unit coupled to the base of the apparatus, where the control unit is configured to manage and control operation of the scent component devices.

In another aspect of the present disclosure, the control unit of the apparatus may be further configured to include a machine learning unit for learning about the surrounding environment and automatically adjusting the operation of the scent component devices in response to change in the surrounding environment.

In another aspect of the present disclosure, the apparatus may be further configured to include one or more security monitoring devices, which are configured to be controlled via a wireless connection.

In another aspect of the present disclosure, each scent component device may include a plurality of Light Emitting Diodes (LEDs) disposed in the first portion of the scent component device.

In an aspect of the present disclosure, the apparatus may be configured to include one or more speakers coupled to the base for producing an audio output. The one or more speakers may be controlled by a user device over a wireless connection.

In an aspect of the present disclosure, turning on or off operation of the plurality of LEDs of the scent component devices may be coordinated with reproduction of the audio output by the one or more speakers.

In another aspect of the present disclosure, the plurality of LEDs may include LEDs of different colors and are controlled by the user device over the wireless connection.

In an aspect of the present disclosure, the one or more security monitoring devices may include one or more surveillance cameras.

In another aspect of the present disclosure, the base of the apparatus may include a control device configured to control and manage the scent component devices for intelligent autonomous operation of the scent component devices, in response to a change in the surrounding environment.

In another aspect of the present disclosure, the control device of the apparatus may be further configured to include a wireless communication module for communications with a remote device over wireless connections.

In another aspect of the present disclosure, the one or more speakers may be further configured to reproduce a variety of nature sounds including bird chirping, waterfall, winds, or the like.

As such, the implementation of one or more aspects of the present technology may provide numerous benefits to people through provisioning artificial trees and/or plants with more enhanced features.

BRIEF DESCRIPTION OF THE DRAWINGS

A more detailed understanding may be obtained from the following descriptions in conjunction with the following description, appended claims, and accompanying drawings.

DETAILED DESCRIPTION

Figure 1:
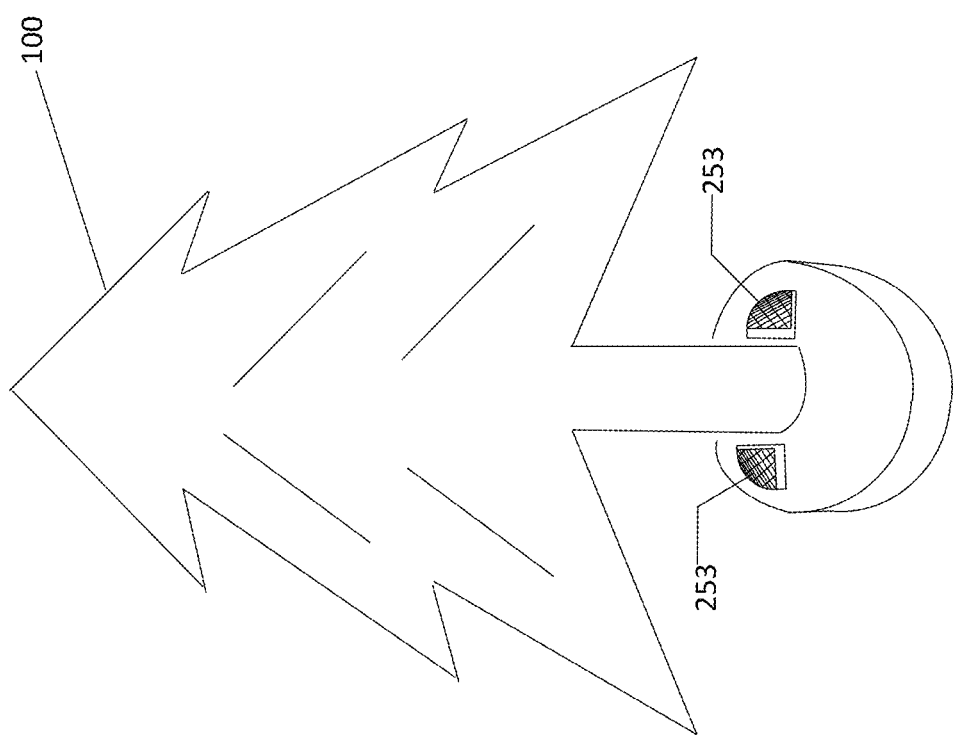
FIG. 1 illustrates an example embodiment of the present technology in accordance with an aspect of the present disclosure.

The detailed description of illustrative examples will now be set forth below in connection with the various drawings. The description below is intended to be exemplary and in no way limit the scope of the claimed invention. It provides a detailed example of possible implementation(s) and is not intended to represent the only configuration in which the concepts described herein may be practiced. As such, the detailed description includes specific details for the purpose of providing a thorough understanding of various concepts, and it is noted that these concepts may be practiced without these specific details. In some instances, well known structures and components are shown in block diagram form in order to avoid obscuring such concepts. It should be noted that like reference numerals are used in the drawings to denote like elements and features.

While the methodologies are described herein sometimes as a series of steps or acts, for the purpose of simplicity, it is to be understood that the claimed subject matter is not limited by the order of these steps or acts, as some steps or acts may occur in different orders and/or concurrently with other acts from that shown and described herein. Further, not all illustrated steps or acts may be required to implement various methodologies according to the present technology disclosed herein. Also, it should be appreciated that the apparatus and methods described herein may be utilized separately or in combination with other aspects of the present disclosure, or in combination with conventional technology, without departing from the teachings of the present disclosure.

FIG. 1 illustrates an exemplary embodiment of the present technology in accordance with an aspect of the present disclosure. By way of example, in an aspect of the present disclosure, FIG. 1 shows an artificial tree 101 including one or more aspects of the present technology disclosed herein. The exemplary embodiment provides an apparatus in the form of an artificial pine tree that can be used as a Christmas tree with enhanced features during the joyful holiday season.

Figure 2:
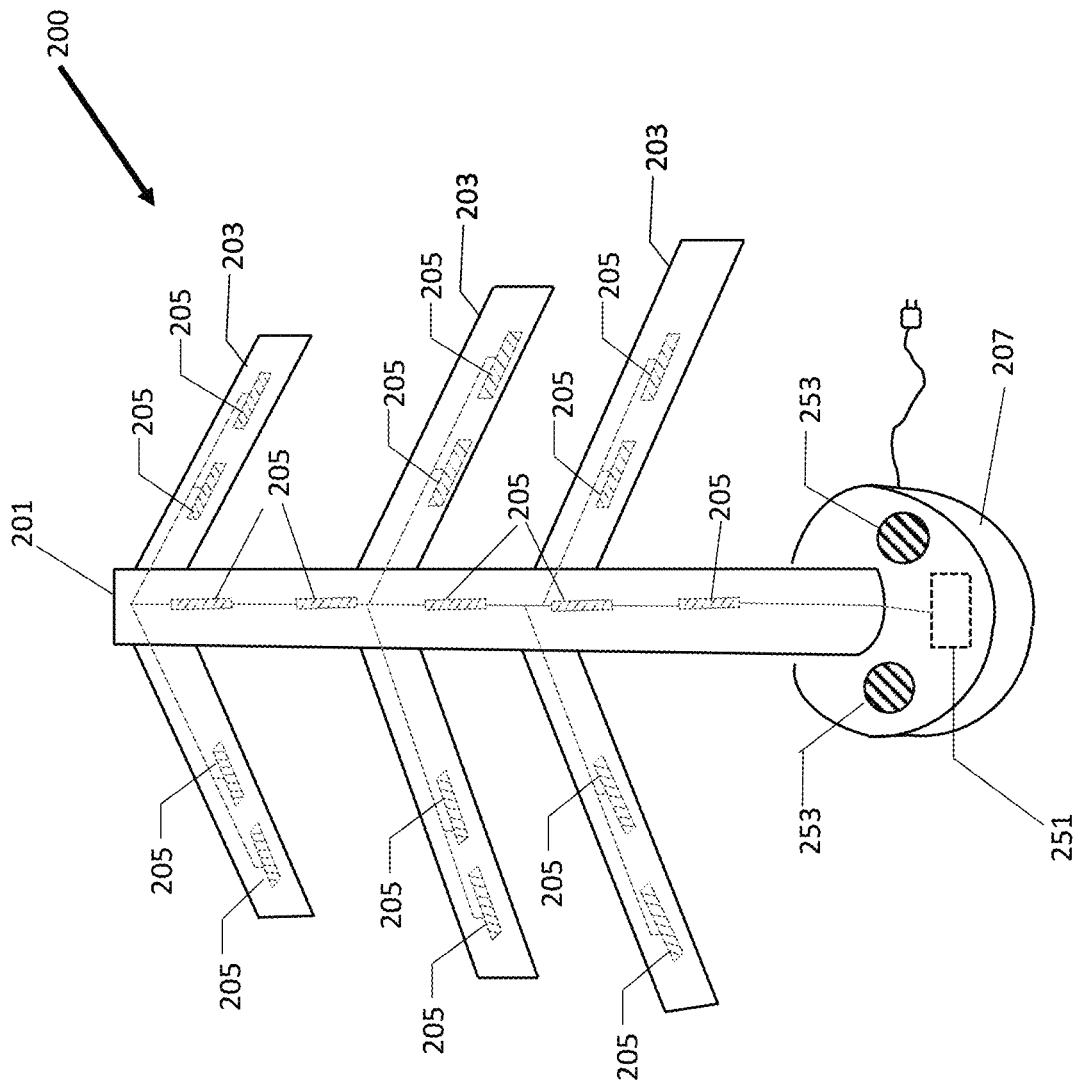
FIG. 2 illustrates an example stem structure of the embodiment of FIG. 1 in accordance with an aspect of the present disclosure.

FIG. 2 illustrates an exemplary embodiment of a stem structure without leaf components for the artificial tree or apparatus shown in FIG. 1. By way of example, a stem structure 200 of the apparatus shown in FIG. 1 is configured to include a base 207, a main trunk body 201 coupled to the base 207, a plurality of branches 203 coupled to the main trunk body 201, and a control unit 251 coupled to the base 207. Further, the main trunk body 201 and/or one or more branches 203 are configured to include one or more receiving portions or scent component receptacles 205. In the example, a plurality of scent component devices may be disposed in the one or more scent component receptacles 205. Further, the one or more scent component receptacles 205 and the control unit 251 may be electrically connected via wires and/or electrical contacts for control as well as power supply purposes. That is, via wires and electrical contacts, each scent component receptacle 205 may receive power and data from the control unit 251. In the example, the plurality of scent component devices may be configured to be removable and each scent component device may include one or more electrical contacts which correspond to electrical contacts disposed inside an inside portion of the receiving portion or scent component receptacle 205 of the main truck body or branches.

Further, in another aspect of the present disclosure, the example may further include one or more speakers 253 that are coupled to the base 207. The one or more speakers 253 may be wired or wireless speakers that may be configured to communicate with the control unit 251 or a remote device (not shown) over a network.

In the example of FIG. 2, the control unit 251 may be configured to perform various functions, including functions to control the one or more scent component receptacles 205, control the one or more speakers 253, one or more scent component devices 215, and/or perform functions of machine learning of an environment and control various devices disposed or coupled to the apparatus 200. In another aspect of the present disclosure, the various devices may include different types of environmental sensors, for example, temperature sensors, humidity sensors, image sensors, or surveillance cameras or other devices.

In an aspect of the present disclosure, the control unit 251 may be configured to communicate with a remote device or a personal communication device, such as a mobile device for monitoring and/or control of various functions or features of the apparatus. In one implementation, a user application may be installed on a mobile device and may be used to control the scent component devices 215 for controlling and/or managing an amount of scent being produced, released, or diffused in a given area where the apparatus is disposed. The amount of scent produced, released, or diffused may be automatically adjusted based on a number of people present in the space, or alternatively, based on human traffic density over time in which machine learning or artificial intelligence techniques may be employed to collect data, perform needed analysis of the collected data, and take subsequent actions based on the analysis.

Further, in another aspect of the present disclosure, the base 207 of the apparatus 200 may also include an electrical cord for supplying power to various components of the apparatus 200. The electrical cord may be plugged into an electrical outlet. In another aspect of the present disclosure, the base 207 of the apparatus may include one or more rechargeable battery units for supplying power to the various components of the apparatus 200.

Figure 3:
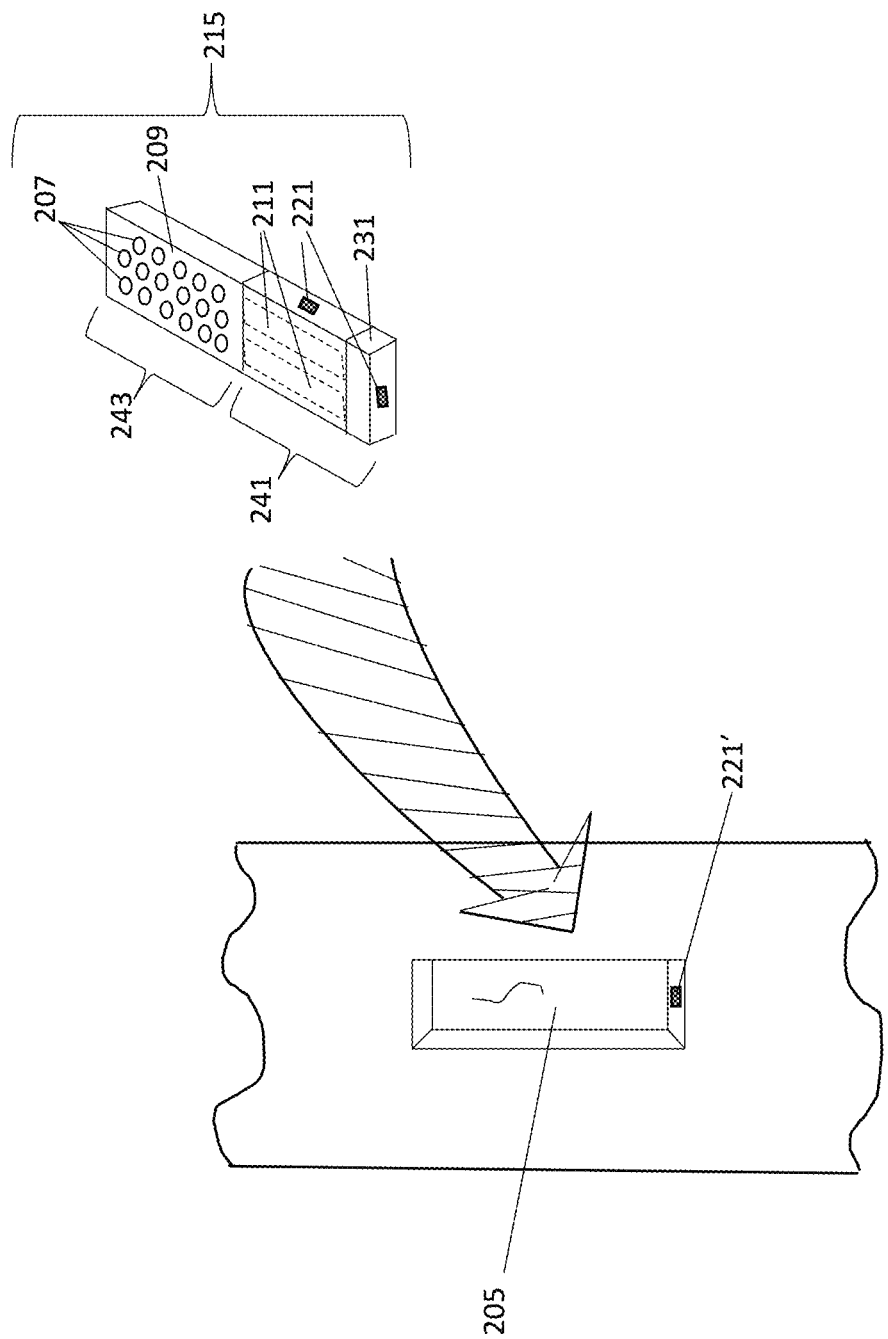
FIG. 3 illustrates an example embodiment of the present technology in accordance with an aspect of the present disclosure.

FIG. 3 illustrates an example embodiment of the present technology in an aspect of the present disclosure, conceptually illustrating a portion of the main trunk body 201 or branch 203 as well as an example scent component device 215. FIG. 3 shows that the scent component device 215 is configured to be inserted into a receiving space of the scent component receptacle 205. As shown in FIG. 3, the scent component receptacle 205 may include one or more electrical contacts 221 inside the receiving space of the scent component receptacle 205 for electrical contact with the scent component device 215. That is, when the scent component device 215 is inserted into the receiving space of the scent component receptacle 205, electrical contacts are made.

In an aspect of the present disclosure, the scent component device 215 may be configured to include multiple portions or parts, for example, a first portion 241 and a second portion 243 each including different functions and/or parts. The first portion of the scent component device 215 may include one or more scent cartridges 211 containing a scent material, a control unit 231, and one or more electrical contacts 221 disposed on a bottom or sides of the scent component device 215. It is noted that positions of the one or more electrical contacts 221 of the scent component device 215 are in alignment with positions of the one or more electrical contacts 221' of the scent component receptacle 205 so that electrical contact is made with each other. Further, the second portion of the scent component device 215 may include a plurality of diffuser holes 207 as well as supporting guides 209 for the purpose of diffusing or releasing the scent from the one or more scent cartridges in the scent component device 215. A group of the plurality of diffuser holes 207 may be opened or closed according to command and control of a control unit 231 or the control unit 251 to control the amount of the scent released into a surrounding environment.

Referring back to FIG. 3, as mentioned above, the first portion of the scent component device 215 may include one or more scent cartridges 211, the control unit 231, and one or more contacts 221 disposed on the bottom and/or side of the scent component device 215. Although the example of FIG. 3 shows the scent cartridges 211 in a rectangular form, the shapes of the scent cartridges 211 may not be limited thereto and other variations are possible. Further, the scent cartridges 211 may be configured to include the same scent material or different scent materials in each cartridge.

In an aspect of the present disclosure, the control unit 231 may be configured to control and manage timings of the release of scent, as well as determine a requisite amount of scent needed from the one or more scent cartridges 211. In addition, the control unit 231 may also be configured to include a wireless transceiver to perform communications with other devices, including but not limited thereto, such as a remote device over a network. In one implementation, the control unit 231 may be configured to communicate with the remote device via WiFi, Bluetooth, cellular, or other wireless technologies. Further, in another aspect of the present disclosure, the control unit 231 may be configured to communicate with the control unit 251 disposed in the base 207 of the apparatus 200 shown in FIG. 2.

Referring back to FIG. 3, when the scent component device 215 is inserted into the scent component receptacle 205 and activated, the scent component device 215 may be operable to disperse or release a specific scent, e.g., pine scent or the like, into a surrounding environment in which the apparatus is disposed. Further, release timings or frequency of release of the scent may be controlled by the control unit 231 or 251 as well as the remote device over the network.

In an aspect of the present disclosure, the scent component device 215 may include a scent in the form of liquid or solid, e.g., a solid stick or the like. By way of example, in one implementation, when the scent is in the form of liquid, it may be in a cartridge form as in a common scent diffuser. In another implementation, when the scent is in the form of solid, it may include a heating element disposed inside the scent component device 215. In the example, a heating element may be disposed in the first portion of the scent component device 215 and/or the second portion of the scent component device 215, in such a way that the solid scent may melt as the diffuser or the scent component device 215 is in operation. Alternatively, in the case of solid scent, it is also possible to use a method of other solid scent air fresheners. It is noted that various scent release approaches may be used by one skilled in the art.

Further, in one implementation, the second portion of the scent component device 215 may include one or more heating elements for the purpose of diffusing or releasing the scent through the diffuser holes 207. In another aspect of the present disclosure, the scent component device 215 may include a small scale ultrasonic based diffusing mechanism for the purpose of diffusing the scent. It is also noted that other techniques or methodologies may be used for releasing the scent into a surrounding environment.

As mentioned above, in the example disclosed herein, the electrical contacts 221 and 221' are used to make electrical connections between the scent component receptacles 205 and the scent component devices 215. The electrical contacts 221 are configured to be in contact with electrical contacts 221' of the scent component receptacles 205, which are used for power to be supplied to the scent component devices 215 for operation of various components including the diffuser and electronics thereof. When in full operation, as shown in FIG. 2, the scent component devices 215 and controller may be electrically connected via the electrical contacts.

In another aspect of the present disclosure, for the purpose of controlling an amount of scent being released into the surrounding environment, the number of open diffusing holes 207 may be determined and controlled by the control unit 251 or 231 and/or a remote device including a user device 501. The diffusing holes 207 may be configured to open or close. In one implementation, one or more profiles of the environment, but not limited thereto, including collected sensor data may be used to determine the number of open diffusing holes 207 for a requisite release amount of the scent. Further, certain timings of the release of the scent may be controlled by the control unit 251 or 231 and/or the remote device including the user device 501; for example, the release of scent may be made every 5 minutes, 10 minutes, etc. for a predetermined duration.

Figure 4:
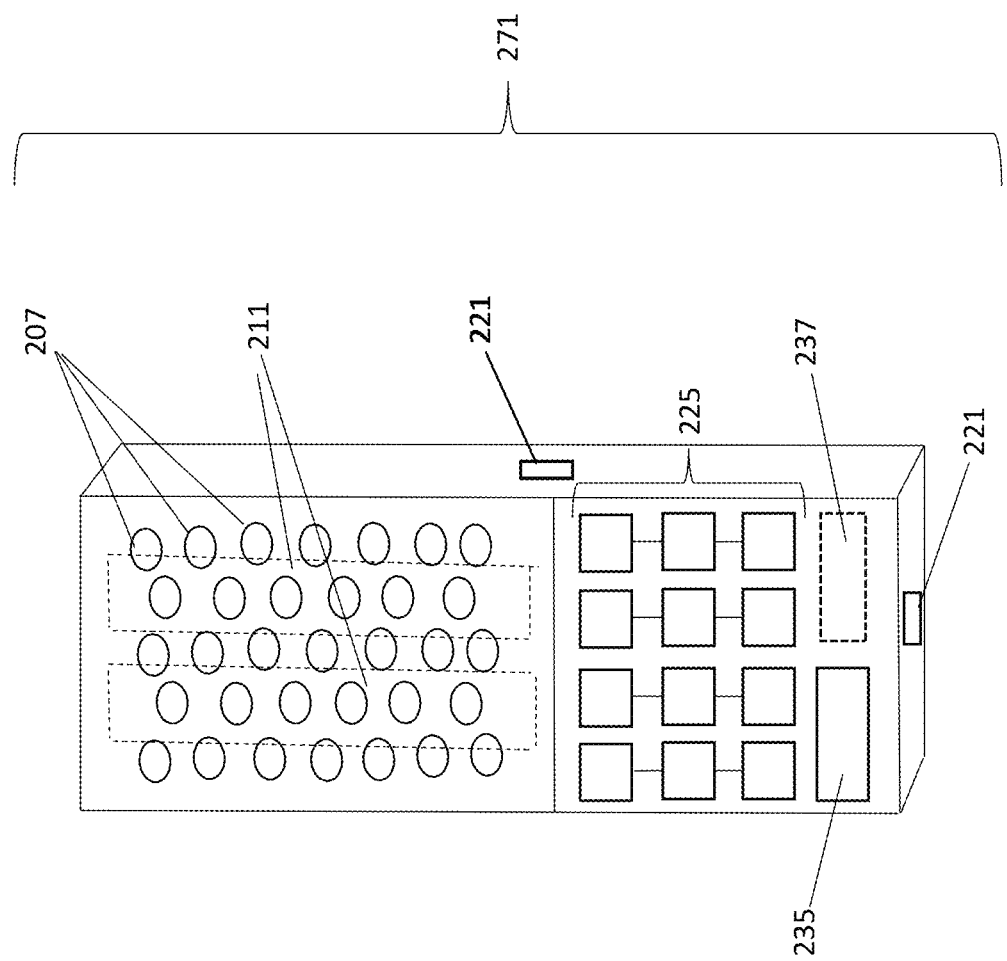
FIG. 4 illustrates another example embodiment of the present technology in accordance with an aspect of the present disclosure.

FIG. 4 illustrates another embodiment of the present technology in accordance with an aspect of the present disclosure. In one implementation, the scent component device 271 may include a plurality of diffuser holes 207, a plurality of scent cartridges 211, a plurality of light emitting diodes (LEDs) 225, and a LED control 235. In an aspect of the present disclosure, the scent component device 271 may optionally include a transceiver 237 for wireless communications with a remote device over a wireless network. In the example, the plurality of LEDs 225 may be configured to turn on or off in accordance with operational commands received from the remote device and/or the control unit 251 coupled to the base 207 of the apparatus as shown in FIG. 2. In an aspect of the present disclosure, the plurality of LEDs 225 may turn on or off in a coordinated manner to produce light displays. The coordination of turning on or off of LEDs 225 may be controlled by the control unit 235 or may be controlled by a remote user device via the wireless transceiver 237. Further, predetermined patterns of turn-on or turn-off of one or more LEDs of a plurality of scent component devices 215 may be used, coordinated and controlled via wireless connections by an application software installed on a remote device including, but not limited thereto, a mobile device, a tablet, a computer, a remote server or the like. The wireless connections may include various wireless communications protocols, such as WiFi, Bluetooth, Infrared, near field communications (NFC), short range communication protocols, cellular wireless protocols, or the like.

Figure 5:
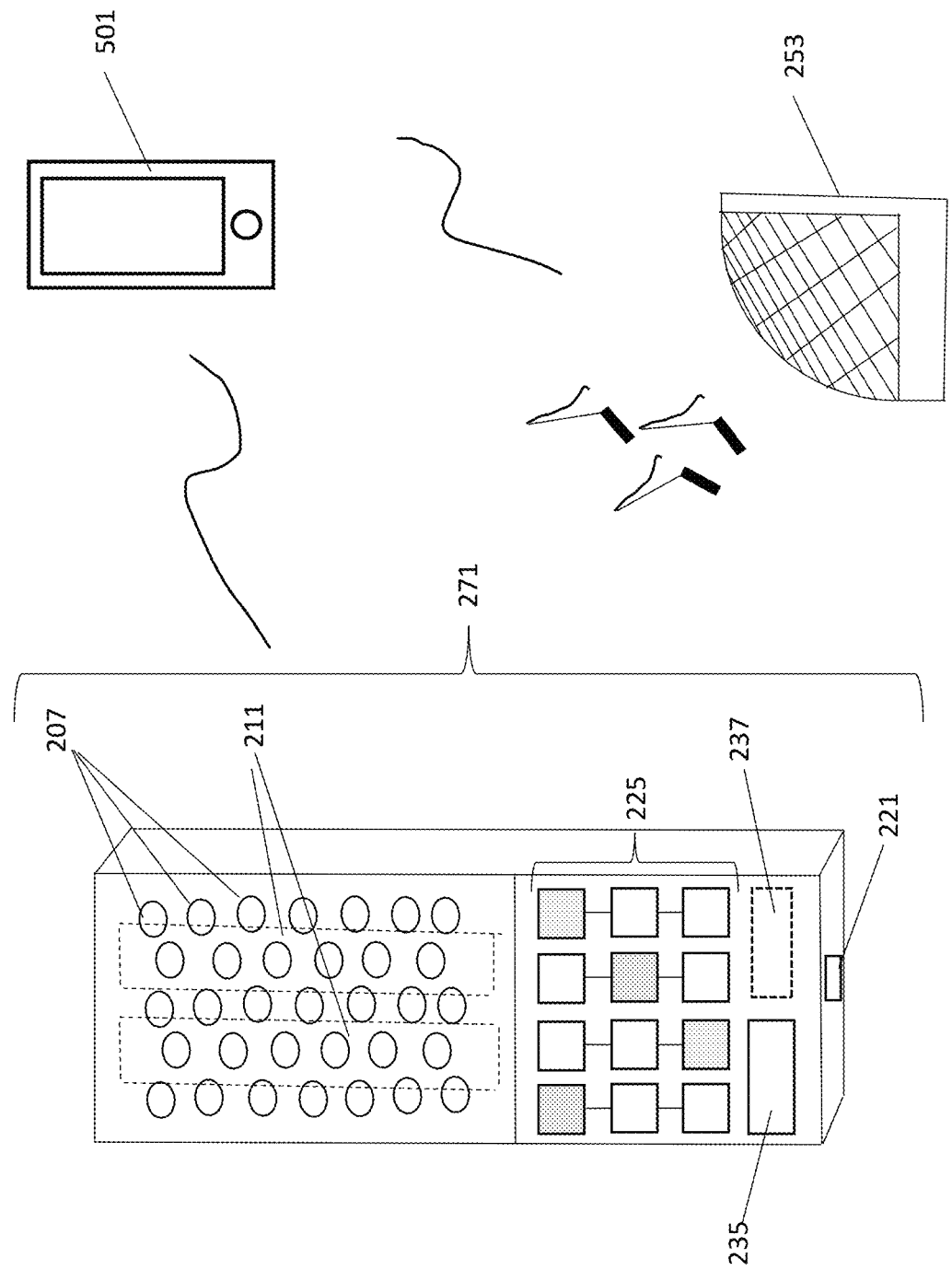
FIG. 5 illustrates an example embodiment of the present technology in accordance with an aspect of the present disclosure.

FIG. 5 is an illustrative example of an embodiment of the present technology in an aspect of the present disclosure. FIG. 5 illustrates an example case that a plurality of LEDs 225 of a scent component device 271 may be turned-on or -off in conjunction or cooperation with a music piece being played through one or more speakers 253. The turning-on or -off of the LEDs as well as the playing of the music piece may be controlled by a user device 501 over a wireless network. Also, in the example, the scent may also be released from the one or more scent cartridges 211 through the diffuser holes 207 based on certain characteristics of the rhythm or tune of the music piece. The release of scent may be coordinated or timed in accordance with the musical rhythms of the music piece being played. Further, the plurality of LEDs 225 may include LEDs of different colors and be turned-on or -off in accordance with one or more predetermined patterns as commanded by the user device 501.

As mentioned, the remote device 501 may be configured to control a plurality of scent component devices 271 or 215 and a plurality of speakers 253. That is, the remote device 501 may wirelessly send command and control data to the scent component devices 215 or 271 for turning-on or turning-off (or changing of colors) of LEDs of the scent component device 215 or 275 in a predetermined pattern and send an audio stream to the one or more speakers 253 for reproducing the audio in one or more coordinated manners while the certain LEDs are turned on or off, as in certain light display shows. In one example, while a certain music piece is played, certain groups of LEDs may be flashed or turned on or off in a predetermined synchronized manner. That is, during a specific occasion (e.g., a birthday event), while the birthday music is played through the one or more speakers 253 of the apparatus 100, select groups of LEDs of the scent component devices 215 or 271 may be flashed at predetermined interval in accordance with various patterns, and a certain scent may be optionally released under the control of the remote device 501. Further, the flashing patterns of the LEDs of the scent component devices 215 or 271, the certain music pieces played through the one or more speakers 253, and the release amount of the scent may also be controlled and/or managed by an application over a network or a user device such as a mobile phone, a tablet, or the like. In this case, the user device may act as a central control device for all the other devices. Further, the plurality of speakers 253 may be detached from the base of the apparatus and be disposed at other locations to suit different purposes or occasions. Further, depending upon the different occasions, different scent may be released into the surrounding environment.

In another aspect of the present disclosure, the apparatus of the present disclosure may further include a humidifier device for an environmental control purpose. By way of example, the base 207 of the apparatus 100 may be configured to include a humidifier and/or a water reservoir for that purpose. In the example, the apparatus of FIG. 1 or FIG. 2 may include one or more sensors, such as humidity sensors, temperature sensors, etc. to determine a level of humidity in the surrounding environment and based on collected data from one or more sensors either disposed on the apparatus or located in the surrounding environment, humidify the area in which the apparatus is disposed. The control unit of the apparatus may communicate with the one or more sensors disposed or located in the surrounding environment. Further, as mentioned above, the artificial tree 101 or the apparatus may be configured to include the control unit in the base of the main trunk body 201 of FIG. 2. The control unit may be configured to wirelessly communicate with one or more external units for control and management of various functions. The various functions may include smart functions such as scent dispensing control and management, humidity level control and management, security monitoring and management, machine learning, etc.

In another aspect of the present disclosure, the apparatus of the present disclosure may further include one or more surveillance cameras which may be disposed on the main trunk body or the branches. The one or more surveillance cameras may be used to monitor people traffic as well as observe different moods of people present around the apparatus in the surrounding environment. Through the one or more surveillance cameras, various data on people in the surrounding environment may be collected and used in operating and/or performing the intelligent release of the scent into the surrounding environment as well as performing appropriate control of the scent component devices, LEDs, and many other components.

Figure 6:
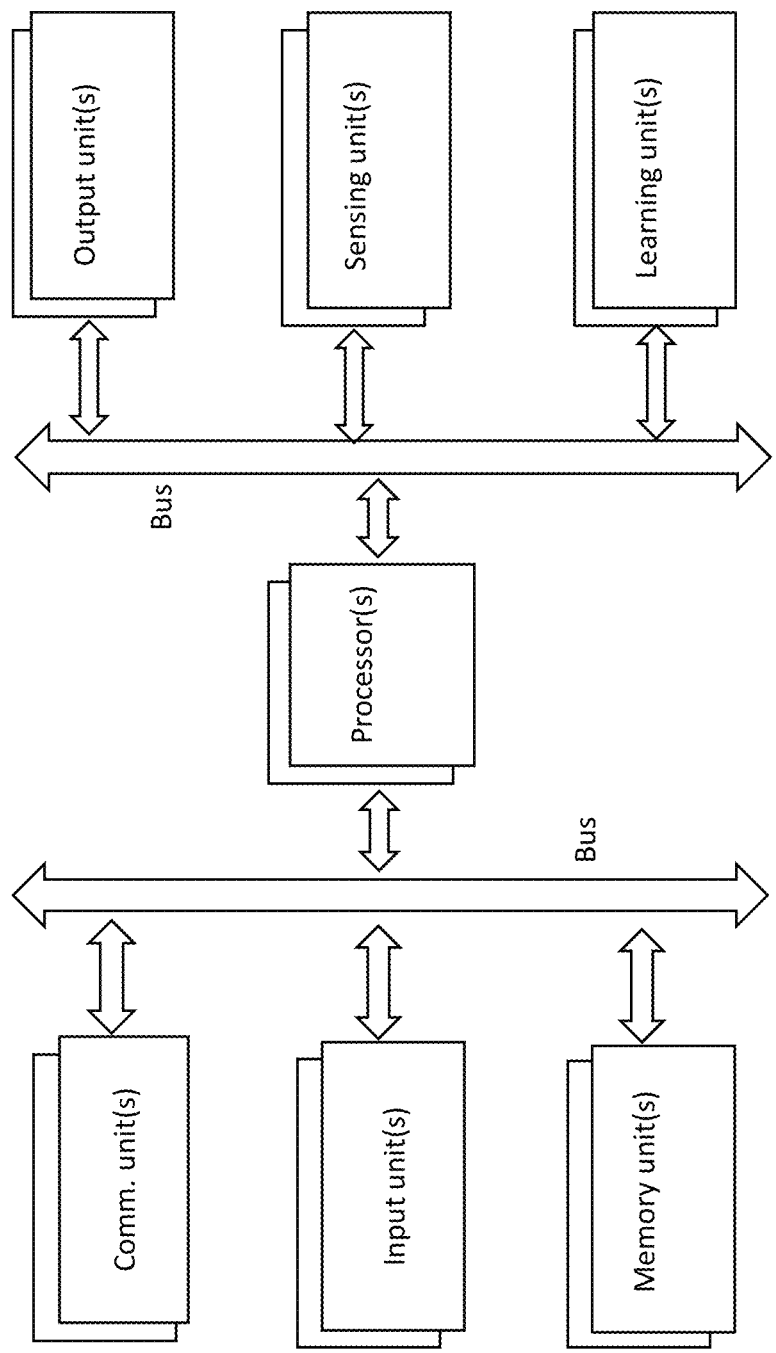
FIG. 6 is a diagram conceptually illustrating an example embodiment of the present technology in accordance with an aspect of the present disclosure.

FIG. 6 conceptually illustrates an example embodiment of a computing device, including but not limited thereto, the control unit 251, 235 disclosed herein. In an aspect of the present disclosure, the apparatus of FIGS. 1-6 may include an embodiment of a computing device of FIG. 6. By way of example, the embodiment may include one or more communication unit(s), one or more input unit(s), one or more memory unit(s), one or more output unit(s), one or more sensing unit(s), one or more learning unit(s), and one or more processor(s), all of which are configured to communicate with each other via one or more bus(es). In the example, the communication unit(s) are configured to transmit and receive data to and from one or more external devices via various communications technology, including but not limited thereto, such as wired and/or wireless communication technologies, e.g., WiFi, Ethernet, fifth generation (5G), wireless local area network (LAN), Bluetooth, radio frequency identification (RFID), near field communications (NFC) and the like. The input unit(s) may be configured to include one or more sensors, cameras, microphones, and/or user inputs. The input unit(s) may also be configured to acquire new raw data based on features extracted from the data processed by the learning unit(s). The learning unit(s) may be configured to learn one or more models, each of which may comprise an artificial neural network by using learned data. In the example, such a learned artificial neural network may be referred to as a learning model. The learning model may be used to infer a value for new input data rather than learning data and the inferred value may be used as a basis for determining to perform a certain operation. Further, the learning model may be built and matured through various artificial intelligence techniques including deep learning techniques and others.

Further, the control unit 251 of the apparatus 100 or 200 as shown in FIG. 1 or FIG. 2 may be configured to work together with one or more learning models. The one or more learning models may be built based on collected data from environmental sensors as control parameters for releasing scent. The one or more learning models may be part of software and/or hardware components of the control unit 251 or reside in distinct computing platforms apart from the control unit 251. In one implementation, as mentioned above, the control unit 251 may learn about a surrounding environment in which the apparatus 100 may be placed and sensory data such as temperature, humidity, an amount of scent diffused, people traffic, people's mood and reaction may be collected as well as inputs by user(s) or remote devices, or the like. A large set of collected data may be collected and inputted into one or more artificial neural networks to build and tune the one or more learned models. Such built one or more learned models can then be used to automatically adjust and/or control the various features of the apparatus, such as setting an appropriate amount of scent being diffused or released, selection of music being reproduced via speakers, selection of patterns of LEDs being displayed, coordination of LEDs being displayed and the music being played, operations of surveillance cameras, or the like. The one or more learned models may be enhanced by communications with the remote device, in particular, communications for receiving command and control as well as management data.

Referring back to FIG. 6, the processor(s) may be configured to perform artificial processing along with the learning unit(s). The learning unit(s) may also be configured to include one or memory unit(s) integrated or integrated in the apparatus, or externally connected to the apparatus. The sensing unit(s) are configured to acquire at least one of internal information, ambient environment, and/or user information that may be inputted via various sensors. The output unit(s) may be configured to generate an output relating to a visual sense, an auditory sense, a haptic sense, or the like. Further, the output unit(s) may be configured to include one or more display unit(s) for outputting various pieces of information, one or more speakers for outputting an audio, etc. The memory unit(s) may be configured to store data for various functions, for example, input data acquired by the input unit(s), learning data, learning models, learning history, and the like. The processor(s) may be configured to determine at least one executable functions based on information determined or generated by one or more data analytic methods or machine learning algorithms.

Further, the processor(s) may be configured to control various components of the embodiment(s) to execute one or more predetermined functions. In an aspect of the present disclosure, the processor(s) may be configured to request, search, receive, or use data of the learning unit(s) or the memory unit(s), as well as control the various components of the embodiment(s), to determine and display on a user's controller interface. Also, the processor(s) may be configured to generate one or more control signals for controlling one or more external devices and may transmit the generated one or more control signals to the one or more external devices. Further, the processor(s) may be configured to receive input information and determine a user's requirements based on the received user input(s). The processor(s) may be configured to collect history information including the operation contents of the embodiment(s) or the user's feedback on the operation and may store the collected history information in the memory unit(s) or the learning unit(s) or transmit the collected history information to external device(s). The collected history information may be used to update the learning models. Furthermore, the processor(s) may be configured to control and manage one or more programs stored in the memory unit(s) and operate one or more components to control and manage the one or more programs.

In another aspect of the present disclosure, various implementations of the present disclosure described herein may be realized in hardware components including digital electronic circuitry, logic components, integrated circuits including Application Specific Integrated Circuits (ASICs), computer hardware, firmware, software, and/or combinations thereof. These various implementations may include implementations in one or more computer programs that are executable and/or interpretable on one or more programmable systems including at least one programmable processor coupled to receive data and instructions from and to transmit data and instructions to a storage system, at least one input device, and at least one output device. The computer programs may include machine instructions for a programmable processor and may be implemented in a high-level procedural and/or object oriented programming language, and/or in assembly or machine language. The terms "machine-readable medium" and "computer-readable medium" as used herein refer to any computer program product(s), apparatus and/or device used to provide machine instructions and/or data to a programmable processor, including a machine-readable medium that receives machine instructions as a machine-readable signal.

As shown above, various methods, techniques, arrangements or their variants may be implemented for artificial trees or plants with capability of producing scent or other features. Other embodiments of the present technology may be possible and are not limited to the disclosed embodiments herein.

Further, it is noted that as used in the specification and the appended claims, the singular forms "a", "an", and "the" include plural referents or one or more items, unless the context clearly indicates otherwise. Also, no element, act, step, or instruction used in the present disclosure should be construed as critical or essential to the present disclosure unless explicitly described as such in the present disclosure. As used herein, except explicitly noted otherwise, the term "comprise" or variations of the term, such as "comprising," "comprises," and "comprised" are not used to exclude other additives, components, integers or steps. The term "first," "second," and so forth used herein may be used to describe various components, but the components are not limited by the above terms. The above terms are used only to discriminate one component from other components, without departing from the scope of the present disclosure. Also, the term "and/or" as used herein includes a combination of a plurality of associated items or any item of the plurality of associated items. Further, it is noted that when it is described that an element is "coupled" or "connected" to another element, the element may be directly coupled or directly connected to the other element, or the element may be coupled or connected to the element through a third element. Also, the term "include" or "have" as used herein indicates that a feature, an operation, a component, a step, a number, a part or any combination thereof described herein is present. Furthermore, the term "include" or "have" does not exclude a possibility of presence or addition of one or more other features, operations, components, steps, numbers, parts or combinations. It is also noted that the foregoing relates only to exemplary embodiments of the present invention or technology and that numerous modifications or alternations may be made therein without departing from the spirit and the scope of the present disclosure as set forth in this disclosure.

Although the exemplary embodiments of the present disclosure are provided herein, the present disclosure is not limited to these embodiments. There are numerous modifications or alternations that may suggest themselves to those skilled in the art. It is appreciated by one skilled in the art that a wide variety of alternate and/or equivalent implementations may be substituted for the specific examples shown and described without departing from the scope of the present disclosure. As such, the exemplary embodiments should not be construed in any way as imposing limitations upon the scope thereof. One the contrary, it is understood that various other embodiments, modifications, and equivalents thereof which, after reading the description herein, may suggest themselves to those skilled in the art without departing from the spirit of the present invention or disclosure and/or the scope of the appended claims.

What is claimed is:

1. An apparatus comprising an artificial tree,
   wherein the artificial tree comprises a base, a main trunk body coupled to the base, a plurality of branches coupled to the main trunk body, and a plurality of scent component devices each coupled to the main trunk body or the plurality of branches,
   wherein the plurality of scent component devices are disposed in receiving portions of the main trunk body or the plurality of branches, and
   wherein each scent component device comprises a body including a first portion and a second portion and a plurality of Light Emitting Diodes (LEDs) are disposed on the first portion.

2. The apparatus of claim 1, wherein the plurality of scent component devices are removable and include electrical contact with an inside portion of the receiving portions of the main trunk body or the plurality of branches.

3. The apparatus of claim 1, wherein the body of each scent component device is configured to be inserted into the receiving portions of the main trunk body or the branches,
   wherein the second portion of the scent component device is configured to receive a scent module including a scent material, and
   wherein when the scent component device is inserted and activated, the scent component device is configured to produce a distinct scent from the scent material, diffusing into an area that the apparatus is disposed.

4. The apparatus of claim 3, wherein the scent module comprises a cartridge form and the distinct scent comprises a pine scent.

5. The apparatus of claim 1 is further configured to include one or more speakers coupled to the base or the main trunk body of the apparatus, wherein the one or more speakers are configured to communicate with a remote device.

6. The apparatus of claim 5, wherein the one or more speakers are wireless speakers capable of communicating with the remote device using WiFi or other wireless communications technology.

7. The apparatus of claim 5 is further configured to include one or more security monitoring devices, wherein the one or more security monitoring devices are configured to be controlled via a wireless connection.

8. The apparatus of claim 7, wherein the one or more security monitoring devices comprise one or more surveillance cameras.

9. The apparatus of claim 5, wherein the one or more speakers are further configured to reproduce a variety of nature sounds including bird chirping, waterfall, winds, or any combinations thereof.

10. The apparatus of claim 1 is further configured to include a control unit coupled to the base of the apparatus wherein the control unit is configured to manage and control operation of scent component devices.

11. The apparatus of claim 10, wherein the control unit is further configured to include a machine learning unit for automatically adjusting the operation of scent component devices in response to a change in a surrounding environment.

12. The apparatus of claim 1 is further configured to include one or more speakers coupled to the base for producing an audio output, and wherein the one or more speakers are controlled by a user device over a wireless connection.

13. The apparatus of claim 12, wherein turn-on or turn-off operation of the plurality of LEDs of the scent component devices is coordinated with reproduction of the audio output by the one or more speakers.

14. The apparatus of claim 13, wherein the plurality of LEDs comprises LEDs of different colors and are controlled by the user device over the wireless connection.

15. The apparatus of claim 1, wherein the base of the apparatus includes a control device configured to control and manage the scent component devices for intelligent autonomous operation of the scent component devices, in response to a change in a surrounding environment.

16. The apparatus of claim 15, wherein the control device is further configured to include a wireless communication module for communicating with a remote device over one or more wireless connections.

\* \* \* \* \*